US008866899B2

(12) United States Patent
Mokichev (10) Patent No.: US 8,866,899 B2
(45) Date of Patent: Oct. 21, 2014

(54) SYSTEMS AND METHODS FOR DEFECT DETECTION USING A WHOLE RAW IMAGE

(75) Inventor: Nickolay Mokichev, San Jose, CA (US)

(73) Assignee: Photon Dynamics Inc., San Jose, CA (US)

( * ) Notice: Subject to any disclaimer, the term of this patent is extended or adjusted under 35 U.S.C. 154(b) by 514 days.

(21) Appl. No.: 13/155,186

(22) Filed: Jun. 7, 2011

(65) Prior Publication Data

US 2012/0314057 A1    Dec. 13, 2012

(51) Int. Cl.
*H04N 7/18* (2006.01)
*G06T 7/00* (2006.01)
*G01N 21/95* (2006.01)

(52) U.S. Cl.
CPC ........ *G06T 7/001* (2013.01); *G01N 2021/9513* (2013.01); *G01N 21/95* (2013.01); *G06T 2207/30121* (2013.01)
USPC ....................................... 348/126

(58) Field of Classification Search
None
See application file for complete search history.

(56) References Cited

U.S. PATENT DOCUMENTS

| 4,983,911 | A | 1/1991 | Henley |
|---|---|---|---|
| 5,774,572 | A | 6/1998 | Caspi |
| 5,774,573 | A | 6/1998 | Caspi et al. |
| 7,177,458 | B1 | 2/2007 | Savareigo et al. |
| 7,212,024 | B2 | 5/2007 | Iwasaki et al. |
| 7,519,222 | B2 | 4/2009 | Kisilev et al. |
| 2004/0032280 | A1* | 2/2004 | Clark et al. .................... 324/770 |
| 2005/0025350 | A1* | 2/2005 | Engelbart et al. ............. 382/141 |
| 2006/0110009 | A1* | 5/2006 | Klassen et al. ................ 382/112 |
| 2008/0075355 | A1 | 3/2008 | Ben-Yishay et al. |
| 2008/0122946 | A1* | 5/2008 | Sung et al. ................. 348/224.1 |

FOREIGN PATENT DOCUMENTS

WO            02/33492 A1    4/2002

OTHER PUBLICATIONS

J. Guzaitis et al., "Image Analysis and Information Fusion Based Defect Detection in Particleboards", Electronics and Electrical Engineering, No. 7(71), ISSN 1392-1215, 2006.
C.H. Lampert et al., "An Optimal Non-Orthogonal Separation of the Anisotropic Gaussian Convolution Filter", Berichte des Fraunhofer ITWM, Nr. 82 (2005), ISSN 1434-9973, Oct. 24, 2005.

* cited by examiner

*Primary Examiner* — Dave Czekaj
*Assistant Examiner* — Kehinde O Abimbola
(74) *Attorney, Agent, or Firm* — TransPacific Law Group; Pavel I. Pogodin, Esq.

(57) ABSTRACT

An apparatus for identifying a defect in an electronic circuit having periodic features, the apparatus including at least a camera for obtaining an image of the electronic circuit and an image processing system. The image processing system receives the image of the electronic circuit from the camera, performs a diagonal shift of the received image of the electronic circuit by at least a diagonal size of the periodic features of the electronic circuit to produce a shifted image of the electronic circuit, identifies a candidate defect using the image of the electronic circuit and the shifted image of the electronic circuit, computes one or more local defect-free reference (golden) images of the electronic circuit using at least one selected area in the closest proximity of the identified candidate defect and determines the defect in the electronic circuit using one or more computed local golden images of the electronic circuit, the image of the electronic circuit.

20 Claims, 4 Drawing Sheets

SYSTEMS AND METHODS FOR DEFECT DETECTION USING A WHOLE RAW IMAGE

BACKGROUND OF THE INVENTION

1. Field of the Invention

The present invention relates generally to the field of electrical inspection of electronic devices and in particular to inspection of Liquid Crystal (LC) and Organic Light Emitting Diode (OLED) displays, the systems used in the inspection and defect detection and techniques for image processing in such systems.

2. Description of the Related Art

Liquid crystal display (LCD) panels incorporate liquid crystals that exhibit electric-field dependent light modulating properties. They are used most frequently to display images and other information in a variety of devices ranging from fax machines, cell phones, tablet and laptop computer screens, to large screen, high-definition TVs. Active matrix LCD panels are complex layered structures consisting of several functional layers: one or more layers of polarizing film; a TFT glass substrate incorporating thin-film transistors, storage capacitors, pixel electrodes and interconnect wiring a color filter glass substrate incorporating a black matrix and a color filter array and a transparent common electrode; an orientation film made of polyimide; and the actual liquid crystal material incorporating plastic/glass spacers to maintain proper LCD cell thickness.

LCD panels are manufactured under highly controlled conditions in a clean room environment to maximize yield. Nonetheless, some LCDs may have to be discarded because of manufacturing flaws in the assembled product.

In order to improve LCD panel production yield, multiple inspection and repair steps are implemented during the entire manufacturing process of LCD panels. Among those, one of the most critical inspection steps is array testing, the electrical inspection step performed at the end of the TFT array fabrication process.

There are several conventional array testing technologies currently available to LCD manufacturers in the market, the most prevalent of them being electrical LCD inspection using electro-optical transducers (modulators) as described, for example, in U.S. Pat. No. 4,983,911, incorporated herein by reference in its entirety. One exemplary LCD inspection device of this type is the Array Checker, commercially available from Photon Dynamics, Inc. an Orbotech company located in San Jose, Calif., USA. In particular, the aforesaid Array Checker inspection system employs a method called "VOLTAGE IMAGING®", which utilizes a reflective liquid-crystal-based modulator configured to measure voltages on individual TFT array pixels. At the time of the inspection of the TFT array by the Array Checker the driving voltage patterns are applied to the TFT panels under test, and the resulting panel pixel voltages are measured by positioning the aforesaid electro-optical modulator in close proximity (typically around 50 microns) to the TFT array under test, and subjecting it to a high voltage square wave voltage pattern. For example, the amplitude of the voltage square wave pattern applied to the modulator could be 300V and frequency of 60 Hz. The electrical potential that is formed across the electro-optical modulator of the inspection system by virtue of its proximity of the pixels of the TFT array under test with applied driving voltage forces liquid crystals in the modulator to change their electric-field-dependent spatial orientation, locally changing their light transmittance across the modulator. In other words, the light transmittance of the modulator becomes representative of the voltages on array pixels in the proximity thereof. To capture the changed modulator transmittance, the modulator is illuminated with a light pulse and the light reflected by the modulator subjected to the panel voltages is imaged onto a voltage imaging optical subsystem (VIOS) camera, which acquires and digitizes the resulting image. The duration of the aforesaid light pulse could be, for example, 1 millisecond. An exemplary system and method for conversion of raw voltage image to LCD pixel map and detection of defects using the map is described in U.S. Pat. No. 7,212,024, incorporated herein by reference in its entirety.

Current methods of defect detection based on voltage imaging use a so-called voltage map, which is a downsampled version of the original image produced by the aforesaid electro-optical modulator and the VIOS camera. The downsampling is customarily performed based on the size, position and geometry of the LCD pixels of the panel, and the accuracy of the resulting defect detection suffers significantly from the inaccuracy of optical calibration of the inspection system as well as other errors such as glass rotation error, system stage drift and the like.

SUMMARY OF THE INVENTION

The inventive methodology is directed to methods and systems that substantially obviate one or more of the above and other problems associated with conventional techniques for inspection of electronic circuits, including PCBs, semiconductor circuits (e.g. on wafers) and in particular LCD and OLED TFT arrays.

In accordance with one aspect of the present invention, there is provided an apparatus for identifying a defect in an electronic circuit having periodic features. The inventive apparatus incorporates a camera for obtaining an image of the electronic circuit and an image processing system comprising a processing unit and a memory. The image processing system is configured to: receive the image of the electronic circuit from the camera; perform a diagonal shift of the received image of the electronic circuit by at least a diagonal size of the periodic features of the electronic circuit to produce a shifted image of the electronic circuit; identify a candidate defect using the image of the electronic circuit and the shifted image of the electronic circuit; compute one or more local defect-free reference (golden) images of an area of the electronic circuit using at least one selected image area containing no defects in the proximity of the identified candidate defect; and determine the presence of a defect in the electronic circuit using the computed golden image of the electronic circuit and a region of the image of the electronic circuit containing the candidate defect.

In accordance with another aspect of the present invention, there is provided a method for identifying a defect in an electronic circuit having periodic features. The inventive method involves: obtaining an image of the electronic circuit using a camera; performing a diagonal shift of the obtained image of the electronic circuit by at least a diagonal size of the periodic features of the electronic circuit to produce a shifted image of the electronic circuit; identifying a candidate defect using the image of the electronic circuit and the shifted image of the electronic circuit; computing one or more local golden images of an area of the electronic circuit using at least one selected image area in the closest possible proximity of the identified candidate defect; and determining the presence of a defect in the electronic circuit using the computed golden image of the electronic circuit and a region of the image of the electronic circuit containing the candidate defect. The aforesaid last three steps are performed by an image processing system comprising the one or more processing units and a memory.

In accordance with a further aspect of the present invention, there is provided a computer-readable medium embodying a set of instructions, which, when executed by one or more processing units of an image processing system, cause the one or more processing units to perform a method for identifying a defect in an electronic circuit having periodic features. The inventive method involving: obtaining an image of the electronic circuit using a camera; performing a diagonal shift of the obtained image of the electronic circuit by at least a diagonal size of the periodic features of the electronic circuit to produce a shifted image of the electronic circuit; identifying a candidate defect using the image of the electronic circuit and the shifted image of the electronic circuit; computing one or more local golden images of an area of the electronic circuit using at least one selected image area in the closest possible proximity of the identified candidate defect; and determining the presence of a defect in the electronic circuit using the one or more computed local golden images of the electronic circuit and a region of the image of the electronic circuit containing the candidate defect. The aforesaid last three steps are performed by an image processing system comprising the one or more processing units and a memory.

The apparatus may include an electro-optical transducer positioned in the proximity of the electronic circuit, wherein a voltage image of the electronic circuit is obtained by imaging the electro-optical transducer onto the camera.

Further improvements may include locating defects in the imaging path and cross-checking the located imaging path defects against the determined defect in the voltage image such that the areas in the voltage image corresponding to imaging path defects are excluded from the detection of defects in the electronic circuit.

Further improvements may include the imaging path defects being located by convolving, using a low pass (e.g. Gaussian) filter, a calibration image of the modulator to obtain the convolved calibration image, computing an absolute difference between the calibration image and the convolved calibration image to obtain a difference image and thresholding the difference image.

Further improvements may include identifying the candidate defect by subtracting the image of the electronic circuit and the diagonally shifted image of the electronic circuit and thresholding the resulting difference image.

Further improvements may include before thresholding, convolving the resulting difference image using a low pass (e.g. Gaussian) filter and performing the thresholding operation on the convolved difference image.

Further improvements may include determining the defect in the electronic circuit by thresholding an image region of interest around the candidate defect using the one or more computed local defect-free reference (golden) images of the area of the electronic circuit.

Further improvements may include determining a defect in the electronic circuit by comparing a difference between the image region of interest around the candidate defect and the computed local golden image of the area of the electronic circuit with a threshold.

Further improvements may include determining the defect in the electronic circuit by comparing the image region of interest around the candidate defect with a first computed golden image comprising minimum intensity values and a second computed golden image comprising maximum intensity values, wherein the minimum and maximum are determined over multiple instances of the golden image.

Additional aspects related to the invention will be set forth in part in the description which follows, and in part will be obvious from the description, or may be learned by practice of the invention. Aspects of the invention may be realized and attained by means of the elements and combinations of various elements and aspects particularly pointed out in the following detailed description and the appended claims.

It is to be understood that both the foregoing and the following descriptions are exemplary and explanatory only and are not intended to limit the claimed invention or application thereof in any manner whatsoever.

BRIEF DESCRIPTION OF THE DRAWINGS

The accompanying drawings, which are incorporated in and constitute a part of this specification exemplify the embodiments of the present invention and, together with the description, serve to explain and illustrate principles of the inventive technique. Specifically.

DETAILED DESCRIPTION

In the following detailed description, reference will be made to the accompanying drawing(s), in which identical functional elements are designated with like numerals. The aforementioned accompanying drawings show by way of illustration, and not by way of limitation, specific embodiments and implementations consistent with principles of the present invention. These implementations are described in sufficient detail to enable those skilled in the art to practice the invention and it is to be understood that other implementations may be utilized and that structural changes and/or substitutions of various elements may be made without departing from the scope and spirit of present invention. The following detailed description is, therefore, not to be construed in a limited sense. Additionally, the various embodiments of the invention as described may be implemented in the form of a software running on a general purpose computer, in the form of a specialized hardware, or combination of software and hardware.

Various aspects of the present invention provide systems and the associated methodology for defect detection in LCD panels, which are not impacted by the factors such as the inaccuracy of optical calibration of the inspection system as well as other errors such as glass rotation error, system stage drift and the like. As the result, inspection systems and methods according to various embodiments of the present invention provide better defect detection performance than the corresponding conventional methods based on voltage maps.

In accordance with one or more embodiments of the invention, the defect detection is conducted from the raw VIOS camera images, including calibration, measurement and voltage images. The voltage images are being calculated from the calibration and measurement images, without scaling them to the LCD system of coordinates (as is being done in the conventional defect detection method described in the aforesaid U.S. Pat. No. 7,212,024). Areas of the calibration image representing damaged areas of the modulator, which need to be excluded from the LCD defect detection, are identified by any well known methods of image non-uniformity detection.

Figure 1:
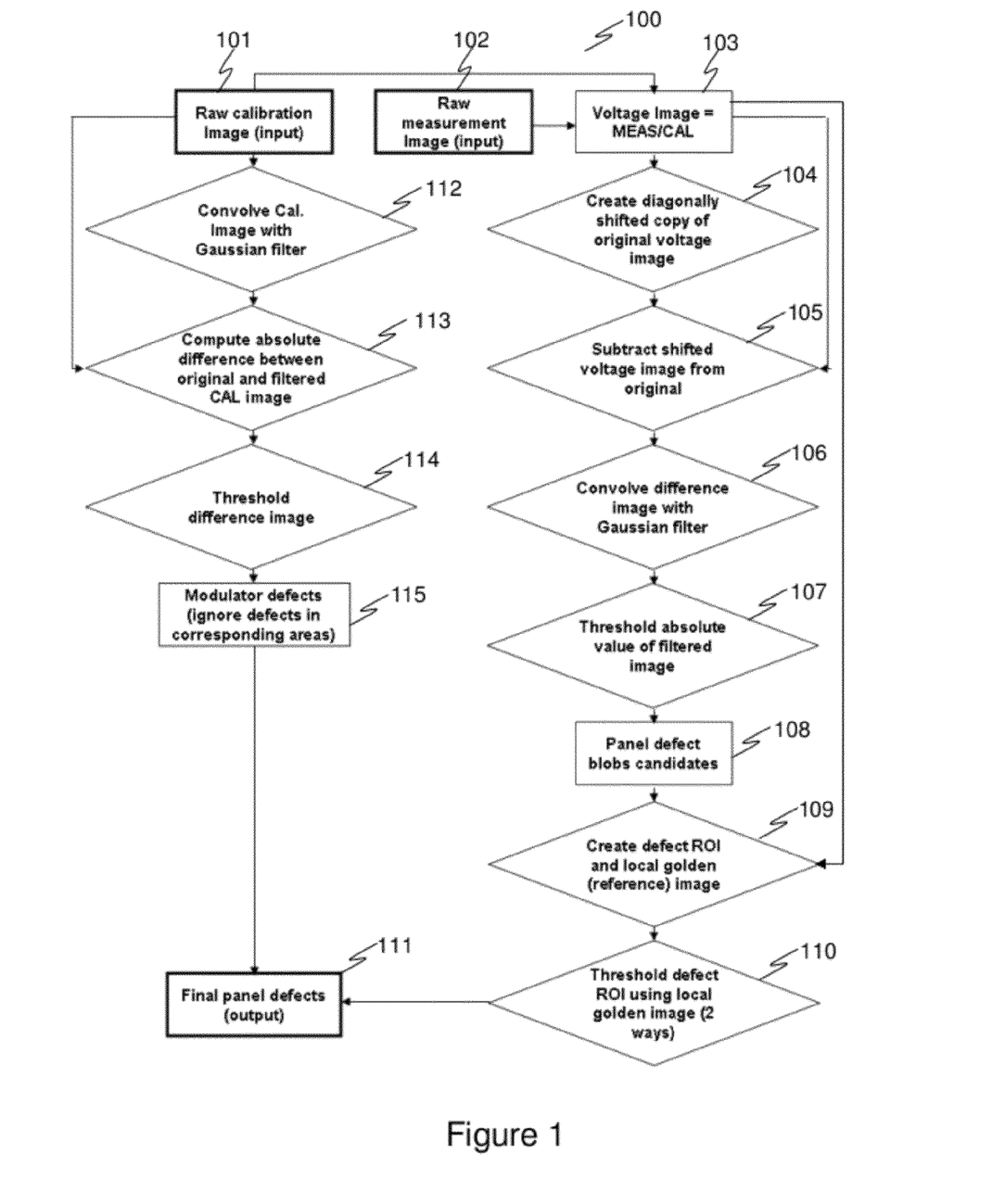
FIG. 1 illustrates an exemplary flowchart of the raw voltage image defect detection algorithm in accordance with one or more embodiments of the inventive concept.

Aspects of the present invention provide systems and methods that utilize the method of thresholding the absolute values of the difference between the original calibration image and the result of the convolution of said image with a Gaussian or other low pass filter. In accordance with one or more embodiments of the invention, the areas of possible LCD defects in the VIOS camera image, which may include, without limitation, image features like dots, clusters of dots, lines, mura defects and the like, are identified and classified using one or more of the following inventive steps, which will be described in connection with FIG. 1 illustrating an exemplary flowchart 100 of the raw voltage image defect detection algorithm in accordance with one or more embodiments of the inventive concept.

In accordance with one or more embodiments of the invention, at step 104, the voltage image generated by the aforesaid VIOS camera is shifted diagonally by the diagonal size of exactly one repeatable element of the inspected device, which is equivalent to the combination of the horizontal and vertical shift of the aforesaid image by the width and height, respectively, of the aforesaid one repeatable element. In accordance with one or more embodiments of the invention, the voltage image is determined at step 103 by normalizing (dividing) the raw measurement image 102 by raw calibration image 101.

In one or more embodiments of the invention, and depending on the structure of the electronic device being inspected, the aforesaid one repeatable element may be a single LCD pixel or a group of LCD pixels, if the electrical and/or geometrical repetition unit is larger than a singe pixel. It should be noted that the inventive concept is not limited to inspection of electronic devices with LCD pixels and, accordingly, the aforesaid repeatable element may be any repetitive structure of the inspected electronic device depending on the type and properties thereof. Likewise, the inventive concept is not limited only to the diagonal shifting of the voltage image by the diagonal size of exactly one repeatable element. In one or more embodiment, the image may be shifted by a first number of repeatable elements horizontally and a second number of repeatable elements vertically, wherein the first and second numbers of repeatable elements may be any integer numbers, including zero. Thus, the term diagonal as used in the context of the present invention was intended to cover all such shifts as well. Also, the aforesaid shift may be accomplished either in one diagonal motion or in consecutive horizontal and vertical motions, which may be performed in any order.

It should be noted that in most voltage imaging inspection systems, the pitch of the imaged LCD pixels in a voltage image generated by the VIOS camera is not an integer multiple of the pixel size of the VIOS sensor, which was used to generate the aforesaid voltage image. Accordingly, in one or more embodiments of the invention, the diagonal image shift described hereinabove should be performed with sub-pixel accuracy, using methods well known to those skilled in the art.

Figure 2:
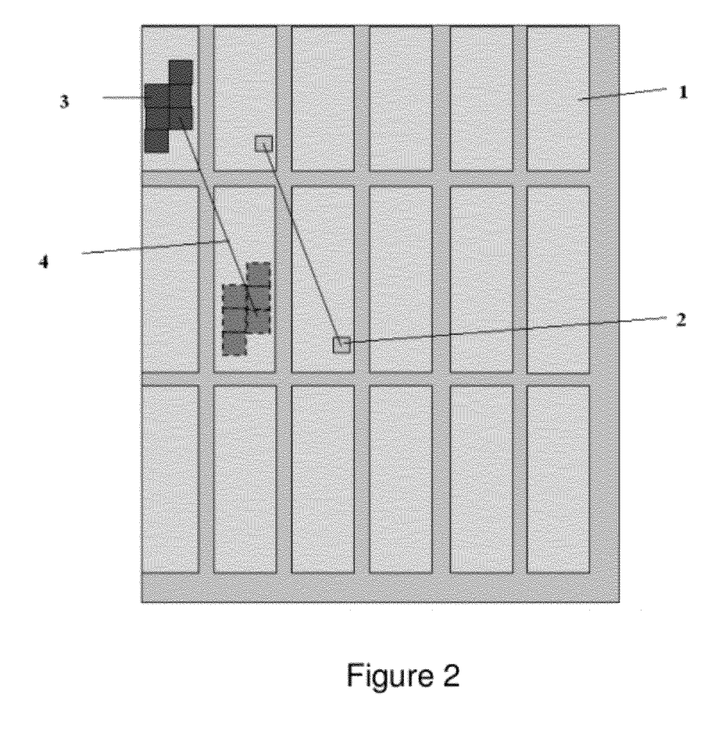
FIG. 2 provides an exemplary illustration of the defect candidate detection in accordance with one or more embodiments of the inventive concept.

In accordance with one or more embodiments of the inventive concept, the shifted copy of the voltage image is subtracted from the original voltage image in step 105 of FIG. 1. As would be appreciated by those of skill in the art, the aforesaid subtraction of the diagonally shifted voltage image from the original voltage image efficiently removes from the resulting image the signal caused by repeating (periodic) features of the voltage images, such as LCD pixels and the driving and addressing (data and gate) lines connected to them, leaving strong signals due to non-periodic defects. As would be appreciated by those of skill in the art, periodic features of the inspected device would create substantially the same signals in substantially the same locations of both the original voltage image and the shifted voltage image, due to the fact that the image is shifted exactly by the diagonal size of one periodic element. Subtracting the aforesaid two images would result in the periodic signals being cancelled out due to the fact that substantially the same periodic signals overlap in the two aforesaid images. On the other hand, non-periodic features, such as defects, would not be cancelled out by the shift and subtraction and would produce two artifacts of opposite polarity in the resultant image. The aforesaid two artifacts from non-periodic features (candidate defect blob and its duplicate) would be displaced with respect to one another by the vector representing the image shift, as shown by numeral 4 in FIG. 2, which provides an exemplary illustration of an embodiment of the inventive defect candidate detection technique. In that figure, large rectangles 1 represent LCD pixels of the tested panel, small squares 2 represent pixels of the VIOS camera, and lines 4 connect identical pixels of the resultant image. The areas 3 delineate a candidate defect blob and its diagonally shifted duplicate.

It should be also noted that the diagonal image shift in accordance with one or more embodiments of the inventive concept allows the detection of all areas of possible defects including vertical (horizontal) line defects in the voltage image with a single shift, which would have been undetected if only vertical (horizontal) image shift was performed.

In accordance with one or more embodiments of the inventive concept, after the aforesaid image subtraction operation, the resultant difference image is smoothed, at step 106 of FIG. 1, by performing a convolution of the difference image with a Gaussian or other low pass filter in accordance with techniques well known to persons of ordinary skill in the art.

In accordance with one or more embodiments of the inventive concept, after the image convolution operation, at step 107, pixel blobs corresponding to possible defects (defect blob candidates 108) are detected by thresholding the absolute value of the convoluted/filtered image obtained in step 106. It should be noted that in accordance with one or more embodiments of the inventive concept, the value of the threshold used in this operation is selected experimentally to assure both selectivity and specificity of the candidate defect detection. In another embodiment, the threshold value may be determined automatically using an iterative algorithm. As would be appreciated by persons of ordinary skill in the art, in general, the value of the threshold would depend on the design and properties of the inspected electronic device as well as customer requirements.

Figure 3:
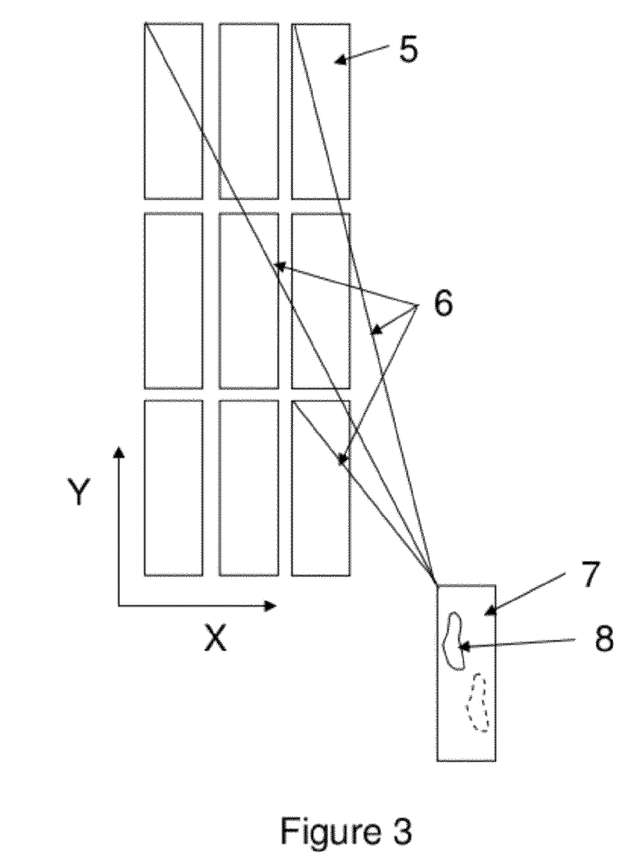
FIG. 3 provides an exemplary illustration of final defect detection and feature extraction in accordance with one or more embodiments of the inventive concept.

In accordance with one or more embodiments of the inventive concept, the next stage of the inventive technique involves final defect detection and feature extraction for classification. Specifically, at step 109 of FIG. 1, for each pair of candidate blobs representing a real defect and its diagonally shifted copy, a region of interest (ROI) containing this blob pair is created. One exemplary ROI is illustrated in FIG. 3, and is designated by numeral 7 in that figure. In accordance with one or more embodiments of the inventive concept, the size of the ROI is an integer multiple of the size of the pixels of the VIOS camera described hereinabove.

In addition, in accordance with one or more embodiments of the inventive concept, the aforesaid step 109 involves creation of (a) local defect-free reference image(s), which will be referred to herein as golden image(s). To this end, the inventive system locates one or more areas (tiles) of the raw voltage image, which are free from any defect blob candidates and which are closest to the ROI containing the defect blob candidate to be analyzed. In accordance with one or more embodiments of the inventive concept, one or more local golden images are created using one or more areas (tiles) of the raw voltage image free from detects and located in the closest possible proximity to the analyzed defect. Exemplary areas (tiles) of the raw image useful for golden image construction are illustrated in FIG. 3, and are designated by numeral 5 in that figure.

In other words, for purposes of construction of the golden image, the inventive system picks undistorted (non-defective) local equivalent image areas (tiles) of the same structure and size as the ROI (tile) containing the blob of the defect candidate to be analyzed. In accordance with various exemplary embodiments of the inventive concept, a total of 9, 25 or other number of tiles are selected for the construction of the golden image. As shown in FIG. 3, in one exemplary configuration, the one or more embodiments of the inventive system operate to create a matrix of P×S neighboring tiles in the vicinity of the tile containing the defect candidate, shifted with steps K*N*PitchX and L*M*PitchY with respect to the defect candidate tile in the X and Y directions, respectively, wherein K is an integer raging from 1 to P and L is an integer ranging from 1 to S, wherein M and N are the number of LCD pixels covered by the defect candidate tile in the X and Y direction, respectively and wherein PitchX and PitchY are the periodicities of the structure of the electronic circuit under inspection in the X and Y directions, respectively. In accordance with various exemplary embodiments of the inventive concept, the size of the matrix may be 3×3 or 5×5. However, as would be appreciated by persons of skill in the art, the present invention is not limited to the aforementioned or any other matrix sizes. In fact, the inventive system may use any suitable number of neighboring tiles.

In addition, in accordance with one or more embodiments of the inventive concept, to create an accurate copy of a neighboring tile of the same size as the defective tile, the inventive system is configured to perform a tile image copy with sub-pixel accuracy. Each sensor pixel in every created tile represents the same local coordinate in the periodical LCD structure as the pixels in the defective tile. In accordance with one or more embodiments of the inventive concept, the final local golden image is calculated as an average of the P×S identified tile images. As would be appreciated by persons of skill in the art, the calculated golden image represents image signal from features of average non-defective tile in the vicinity of the defect candidate tile (ROI). Such image signal from features of an average non-defective tile constitutes a background signal for purposes of defect detection and classification in the defect candidate tile (ROI). It should be noted that the candidate tiles for the construction of the golden image should be selected from within the close vicinity of the defect candidate tile (ROI) to substantially eliminate slowly (gradually) varying effects such as non-uniformity of illumination, optics distortion and the like.

In accordance with one or more embodiments of the inventive concept, the generated golden image is utilized in step 110 of FIG. 1 for accurate detection of the defect blob and for calculation of the features of the detected defect. In accordance with one or more embodiments of the inventive concept, the defect blob is determined by calculating the relative difference of the image representing the tile containing the defect candidate and the golden image and comparing said difference with a threshold. Specifically, in one exemplary implementation, it is determined that the VIOS camera pixel with coordinates (i, j) of the defect candidate tile (ROI) belongs to an actual defective blob if the absolute value of the difference between the intensity of the pixel with said coordinates in the defect candidate tile and the golden image tile normalized by the corresponding golden image tile pixel intensity is greater than the value of a predetermined threshold. Otherwise, the pixel (i, j) is considered to be non-defective.

It should be noted that in accordance with one or more embodiments of the inventive concept, the value of the aforesaid threshold used in this operation is selected experimentally to assure both selectivity and specificity of the candidate defect detection. In another embodiment, the threshold value may be determined automatically using an iterative algorithm. As would be appreciated by persons of ordinary skill in the art, in general, the value of the threshold would depend on the design and properties of the inspected electronic device as well as customer requirements.

In accordance with alternative one or more embodiments of the inventive concept, the actual defect blob detection is performed pursuant to the following method. It should be noted that due to the design features of LCD pixel structure, the intensities of the same VIOS sensor pixels in the images of different LCD pixels can vary significantly from one LCD pixel image to another. Thus, based on the aforesaid matrix of P×S samples of the intensity of each VIOS camera pixel corresponding to the selected P×S non-defective (background) tiles, the inventive system is configured to create two golden tile images. One created golden image contains the minimum values of intensity of each VIOS sensor pixel. On the other hand, the other created image contains the maximum values of intensity of each VIOS sensor pixel. The aforesaid two generated golden images are used by the inventive system as a thresholding interval for detection of the defective tile.

In accordance with one or more exemplary embodiments of the inventive concept, the thresholding is accomplished using the following algorithm. Specifically, it is determined that the VIOS camera pixel with coordinates (i, j) of the defect candidate tile (ROI) belongs to an actual defective blob if DefectTileIntensity(i,j)>IntensityMax(i,j)*(1+ThresholdHigh) or DefectTileIntensity(i,j)<IntensityMin(i,j)*(1−ThresholdLow). Otherwise, the pixel (i, j) is considered to be non-defective. In the above formula, DefectTileIntensity(i,j) is the intensity of the (i, j) VIOS camera pixel in the defect candidate tile and IntensityMax(i,j) and IntensityMin(i,j) correspond to the intensities of the (i, j) VIOS camera pixel in the aforesaid two generated golden images. In accordance with one or more exemplary embodiments of the inventive concept, the upper and lower thresholds (ThresholdHigh and ThresholdLow) are different. In alternative embodiments, the aforesaid thresholds are the same.

Again, it should be noted that in accordance with one or more embodiments of the inventive concept, the value of the aforesaid threshold used in this operation is selected experimentally to assure both selectivity and specificity of the candidate defect detection. In another embodiment, the threshold value may be determined automatically using an iterative algorithm. As would be appreciated by persons of ordinary skill in the art, in general, the value of the threshold would depend on the design and properties of the inspected electronic device as well as customer requirements.

It should be noted that the second described exemplary approach to the defect blob detection in accordance with one or more embodiments of the inventive concept operates better in cases where the voltage image intensity shows significant non-uniformities, such as in areas corresponding to gate or data lines, which can cause large variations in VIOS camera pixel intensity from one LCD area to another.

FIG. 3 provides an exemplary illustration of final defect detection and feature extraction in accordance with an embodiment of the inventive concept. Large rectangles 5 represent nine selected tiles neighboring the defect candidate tile 7 containing the defective pixel with defect blob designated by numeral 8. Black lines 6 connect image pixels of identical origin. The selected tiles 5 can be used in construction of golden image(s) in accordance with the techniques described hereinabove.

In accordance with one or more exemplary embodiments of the inventive concept, to eliminate falsely detected defects resulting from imperfections of the electro-optical modulator, the sensor, and the optics, as well as asperities of the chuck on which inspected substrate rests (we collectively call these imperfection "imaging path defects"), a raw calibration image 101 is processed in steps 112-115 to identify and isolate such imperfections. Specifically, at step 112 of FIG. 1, the raw calibration image 101 is smoothed by convoluting the calibration image with a Gaussian filter—or another low pass filter—in accordance with techniques well known to persons of ordinary skill in the art. At step 113, an absolute difference between the original and filtered calibration images is computed. This difference is compared with a predetermined threshold in step 114. In accordance with this comparison, imaging path defects are identified in step 115. Finally, at step 111 defects identified in the in accordance with the voltage image defect detection method described hereinabove are cross-checked against the isolated imaging path defect areas and the defects contained in these areas are disregarded since they may have originated from imperfections in the imaging path.

In accordance with one or more exemplary embodiments of the inventive concept, the foresaid processes for locating defects in the imaging path and detecting defects in the LCD panel are performed by the image analysis circuitry of the inventive system in a parallel manner to achieve higher processing speed.

It should be also noted that the inventive methodology for detecting defects in electronic devices is not limited only to images obtained using the aforesaid voltage imaging technique. Images obtained using any other appropriate image generation method may be used in conjunction with the teachings described herein for purposes of defect identification and classification.

Figure 4:
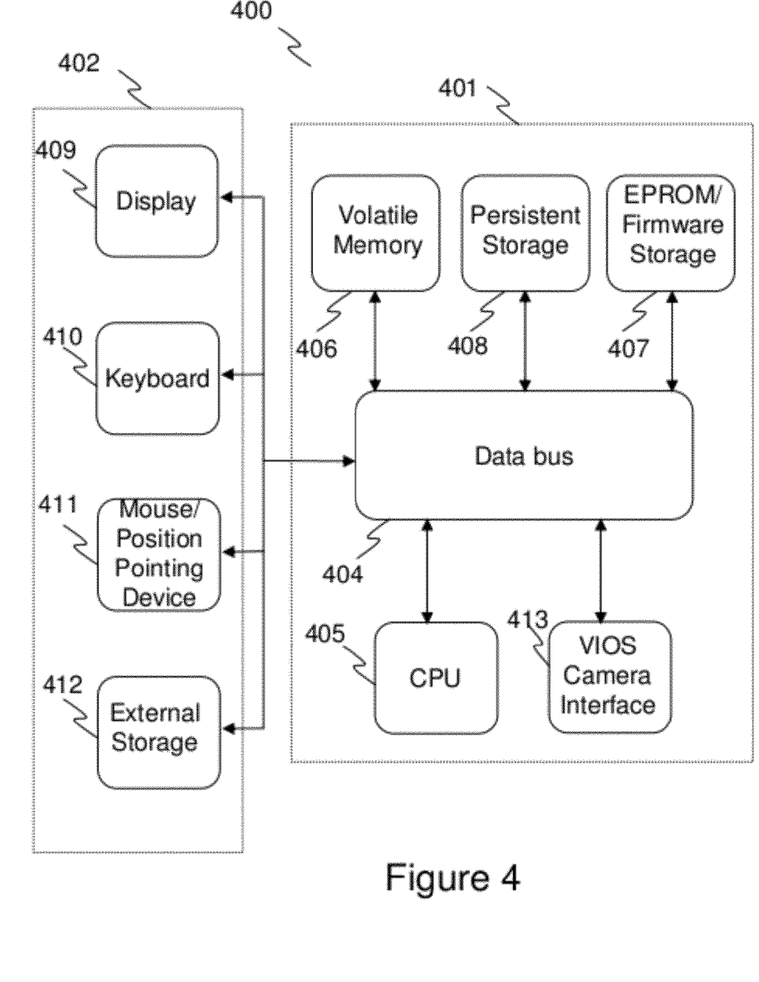
FIG. 4 illustrates an exemplary embodiment of a computerized image processing system upon which the inventive image processing methodology may be implemented.

FIG. 4 illustrates an exemplary embodiment of a computerized image processing system 400 upon which the inventive image processing methodology may be implemented. The system 400 includes a controller 401 and peripheral devices 402.

The controller 401 may include a data bus 404 or other communication mechanism for communicating information across and among various parts of the controller 401, and a processor 405 coupled with bus 404 for processing information and performing other computational, image processing and control tasks, such as image shift and subtraction, thresholding or convolution using the aforesaid low pass (e.g. Gaussian) filter. Controller 401 also includes a volatile memory 406, such as a random access memory (RAM) or other dynamic storage device, coupled to bus 404 for storing various information, including images, as well as instructions to be executed by processor 405. The volatile memory 406 also may be used for storing temporary variables or other intermediate information during execution of instructions by processor 405. Controller 401 may further include a read only memory (ROM or EPROM) 407 or other static storage device coupled to bus 405 for storing static information and instructions for processor 405, such as basic input-output system (BIOS), as well as various system configuration parameters. A persistent storage device 408, such as a magnetic disk, optical disk, or solid-state flash memory device is provided and coupled to bus 404 for storing information and instructions.

Controller 401 may be coupled via bus 405 to a display 409, such as a cathode ray tube (CRT), plasma display, or a liquid crystal display (LCD), for displaying information to a system administrator or user of the controller 401. An input device 410, including alphanumeric and other keys, is coupled to bus 404 for communicating information and command selections to processor 405. Another type of user input device is cursor control device 411, such as a mouse, a trackball, or cursor direction keys for communicating direction information and command selections to processor 405 and for controlling cursor movement on display 409. This input device typically has two degrees of freedom in two axes, a first axis (e.g., x) and a second axis (e.g., y), that allows the device to specify positions in a plane.

An external storage device 412 may be coupled to the controller 401 via bus 405 to provide an extra or removable storage capacity for the controller 401. In an embodiment of the computerized image processing system 400, the external removable storage device 412 may be used to facilitate exchange of data with other computer systems.

The invention is related to the use of the computerized image processing system 400 for implementing the techniques described herein. In an embodiment, the inventive system may reside on a machine such as controller 401. According to one embodiment of the invention, the techniques described herein are performed by the computerized image processing system 400 in response to processor 405 executing one or more sequences of one or more instructions contained in the volatile memory 406. Such instructions may be read into volatile memory 406 from another computer-readable medium, such as persistent storage device 408. Execution of the sequences of instructions contained in the volatile memory 406 causes processor 405 to perform the process steps described herein. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to processor 405 for execution. The computer-readable medium is just one example of a machine-readable medium, which may carry instructions for implementing any of the methods and/or techniques described herein. Such a medium may take many forms, including but not limited to, non-volatile media and volatile media. Non-volatile media includes, for example, optical or magnetic disks, such as storage device 408.

Common forms of computer-readable media include, for example, a floppy disk, a flexible disk, hard disk, magnetic tape, or any other magnetic medium, a CD-ROM, DVD, Blu-Ray Disk, any other optical medium, punchcards, papertape, any other physical medium with patterns of holes, a RAM, a PROM, an EPROM, a FLASH-EPROM, a flash drive, a memory card, any other memory chip or cartridge, or any other medium from which a computer can read.

Various forms of computer readable media may be involved in carrying one or more sequences of one or more instructions to processor 405 for execution. For example, the instructions may initially be carried on a magnetic disk from a remote computer. Alternatively, a remote computer can load the instructions into its dynamic memory and send the instructions over a telephone line using a modem. A modem local to computer system can receive the data on the telephone line and use an infra-red transmitter to convert the data to an infra-red signal. An infra-red detector can receive the data carried in the infra-red signal and appropriate circuitry can place the data on the data bus 404. The data bus 404 carries the data to the volatile memory 406, from which processor 405 retrieves and executes the instructions. The instructions received by the volatile memory 406 may optionally be stored on persistent storage device 408 either before or after execution by processor 405. The instructions may also be downloaded into the controller 401 via Internet using a variety of network data communication protocols well known in the art. The controller 401 also includes a communication interface, such as VIOS camera interface 413 coupled to the data bus 405 and designed to receive image data from the VIOS CCD camera (not shown).

Finally, it should be understood that processes and techniques described herein are not inherently related to any particular apparatus and may be implemented by any suitable combination of components. Further, various types of general purpose devices may be used in accordance with the teachings described herein. It may also prove advantageous to construct specialized apparatus to perform the method steps described herein. The present invention has been described in relation to particular examples, which are intended in all respects to be illustrative rather than restrictive. Those skilled in the art will appreciate that many different combinations of hardware, software, and firmware will be suitable for practicing the present invention. For example, the described software may be implemented in a wide variety of programming or scripting languages, such as Assembler, C/C++, perl, shell, PHP, Java, etc.

Moreover, other implementations of the invention will be apparent to those skilled in the art from consideration of the specification and practice of the invention disclosed herein. Various aspects and/or components of the described embodiments may be used singly or in any combination in the inspection system. It is intended that the specification and examples be considered as exemplary only, with a true scope and spirit of the invention being indicated by the following claims.

What is claimed is:

1. An apparatus for identifying a defect in an electronic circuit having periodic features, the apparatus comprising:
   a. a camera for obtaining an image of the electronic circuit; and
   b. an image processing system comprising a processing unit and a memory, the image processing system being configured to:
   i. receive the image of the electronic circuit from the camera;
   ii. perform a diagonal shift of the received image of the electronic circuit by at least a diagonal size of the periodic features of the electronic circuit to produce a shifted image of the electronic circuit;
   iii. identify a candidate defect using the image of the electronic circuit and the shifted image of the electronic circuit;
   iv. compute one or more local defect-free reference images of an area of the electronic circuit using at least one selected image area containing no defects in the proximity of the identified candidate defect; and
   v. determine the defect in the electronic circuit using the computed defect-free reference image of the electronic circuit and the image of the electronic circuit.

2. The apparatus of claim 1, further comprising an electro-optical transducer positioned in the proximity of the electronic circuit, wherein the voltage image of the electronic circuit created by the camera is obtained by imaging the electro-optical transducer.

3. The apparatus of claim 2, wherein the image processing system is further configured to locate defects in the imaging path and cross-check the located imaging path defects against the determined defect in the voltage image such that the areas in the voltage image corresponding to modulator defects are excluded from the detection of defects in the electronic circuit.

4. The apparatus of claim 2, wherein the imaging path defects are located by convolving, using a low-pass filter, a calibration image of the modulator to obtain the convolved calibration image, computing an absolute difference between the calibration image and the convolved calibration image to obtain a difference image and thresholding the difference image.

5. The apparatus of claim 1, wherein the image processing system is configured to identify the candidate defect by subtracting the image of the electronic circuit and the diagonally shifted image of the electronic circuit and thresholding the resulting difference image.

6. The apparatus of claim 5, wherein before thresholding, the resulting difference image is convolved using a low-pass filter and the thresholding is performed on the convolved difference image.

7. The apparatus of claim 6, wherein a region of interest in the image of the electronic circuit is selected around the candidate defect.

8. The apparatus of claim 1, wherein the image processing system is configured to determine the defect in the electronic circuit by thresholding an image region of interest around the candidate defect using the one or more computed local defect-free reference images of the area of the electronic circuit.

9. The apparatus of claim 1, wherein the image processing system is configured to determine a defect in the electronic circuit by comparing a difference between the image region of interest around the candidate defect and the computed local defect-free reference image of the area of the electronic circuit with a threshold.

10. The apparatus of claim 1, wherein the image processing system is configured to determine the defect in the electronic circuit by comparing the image region of interest around the candidate defect with a first computed defect-free reference image comprising minimum intensity values, determined over multiple instances of the defect-free reference image, and a second computed defect-free reference image comprising maximum intensity values, also determined over multiple instances of the defect free-reference image.

11. A method for identifying a defect in an electronic circuit having periodic features, method comprising:
   a. obtaining an image of the electronic circuit using a camera;
   b. performing a diagonal shift of the obtained image of the electronic circuit by at least a diagonal size of the periodic features of the electronic circuit to produce a shifted image of the electronic circuit;
   c. identifying a candidate defect using the image of the electronic circuit and the shifted image of the electronic circuit;
   d. computing one or more local defect-free reference images of an area of the electronic circuit using at least one selected image area in the closest possible proximity of the identified candidate defect; and e. determining the defect in the electronic circuit using the computed defect-free reference image of the electronic circuit, the image of the electronic circuit, wherein b.-d. are performed by an image processing system comprising a processing unit and a memory.

12. The method of claim 11, wherein the image of the electronic circuit created by the camera is obtained by imaging an electro-optical transducer.

13. The method of claim 11, further comprising locating defects in the imaging path and cross-checking the located imaging path defects against the determined defect in the voltage image such that the areas in the voltage corresponding to modulator defects are excluded from the detection of defects in the electronic circuit.

14. The method of claim 13, wherein the imaging path defects are located by convolving, using a low-pass filter, a calibration image of the modulator to obtain the convolved calibration image, computing an absolute difference between the calibration image and the convolved calibration image to obtain a difference image and thresholding the difference image.

15. The method of claim 11, further comprising identifying a candidate defect by subtracting the image of the electronic circuit and the diagonally shifted image of the electronic circuit and thresholding the resulting difference image.

16. The method of claim 15, wherein before thresholding, the resulting difference image is convolved using a low-pass filter and the thresholding is performed on the convolved difference image.

17. The method of claim 11, further comprising determining the defect in the electronic circuit by thresholding the image region of interest around the defect candidate using the computed defect-free reference image of the area of the electronic circuit.

18. The method of claim 11, further comprising determining the defect in the electronic circuit by comparing a difference between the image region of interest around the defect candidate and the computed defect-free reference image of the area of the electronic circuit with a threshold.

19. The method of claim 11, further comprising determining the defect in the electronic circuit by comparing the image region of interest around the defect candidate with a first computed defect-free reference image comprising minimum intensity values, determined over multiple instances of the defect free-reference image and a second computed defect-free reference image comprising maximum intensity values, also determined over multiple instances of the defect free-reference image.

20. A non-transitory computer-readable medium embodying a set of instructions, which, when executed by one or more processing units of an image processing system, cause the one or more processing units to perform a method for identifying a defect in an electronic circuit having periodic features, method comprising:
 a. obtaining an image of the electronic circuit using a camera;
 b. performing a diagonal shift of the obtained image of the electronic circuit by at least a diagonal size of the periodic features of the electronic circuit to produce a shifted image of the electronic circuit;
 c. identifying a candidate defect using the image of the electronic circuit and the shifted image of the electronic circuit;
 d. computing one or more local defect-free reference images of an area of the electronic circuit using at least one selected image area in the closest possible proximity of the identified candidate defect; and
 e. determining the defect in the electronic circuit using the one or more computed local defect-free reference images of the electronic circuit, the image of the electronic circuit, wherein
 b.-d. are performed by an image processing system comprising the one or more processing units and a memory coupled to the one or more processing units.

* * * * *